United States Patent [19]

Haskell et al.

[11] 4,166,771

[45] Sep. 4, 1979

[54] BUTADIENE RECOVERY

[75] Inventors: Donald M. Haskell, Bartlesville, Okla.; Clarence G. Houser, Indiana, Pa.; Fred T. Sherk, Bartlesville, Okla.

[73] Assignee: Phillip Petroleum Company, Bartlesville, Okla.

[21] Appl. No.: 780,335

[22] Filed: Mar. 23, 1977

[51] Int. Cl.$^2$ .............................................. B01D 3/34
[52] U.S. Cl. ...................................... 203/58; 203/81; 203/82; 203/62; 585/857; 585/864
[58] Field of Search ................. 260/681.5; 203/51, 58, 203/54, 62, 82, 98, 81

[56] References Cited

U.S. PATENT DOCUMENTS

| | | | |
|---|---|---|---|
| 2,360,859 | 10/1944 | Evans et al. | 196/13 |
| 2,371,908 | 3/1945 | Morris | 183/115 |
| 2,382,603 | 8/1945 | Buell | 202/42 |
| 3,436,438 | 4/1969 | Takadeta | 260/681.5 |
| 4,024,028 | 5/1977 | Haskell | 203/51 |

*Primary Examiner*—Hiram H. Bernstein

[57] ABSTRACT

A mixture of C$_4$-hydrocarbons is extractively distilled with sulfolane and acetone or methylethyl ketone as the selective solvent; the rich solvent containing 1,3-butadiene and vinylacetylene is stripped and a small quantity of the ketone is allowed to leave overhead. Thereby the further fractionation of the stripper overhead results in a very efficient separation of 1,3-butadiene and vinylacetylene.

6 Claims, 1 Drawing Figure

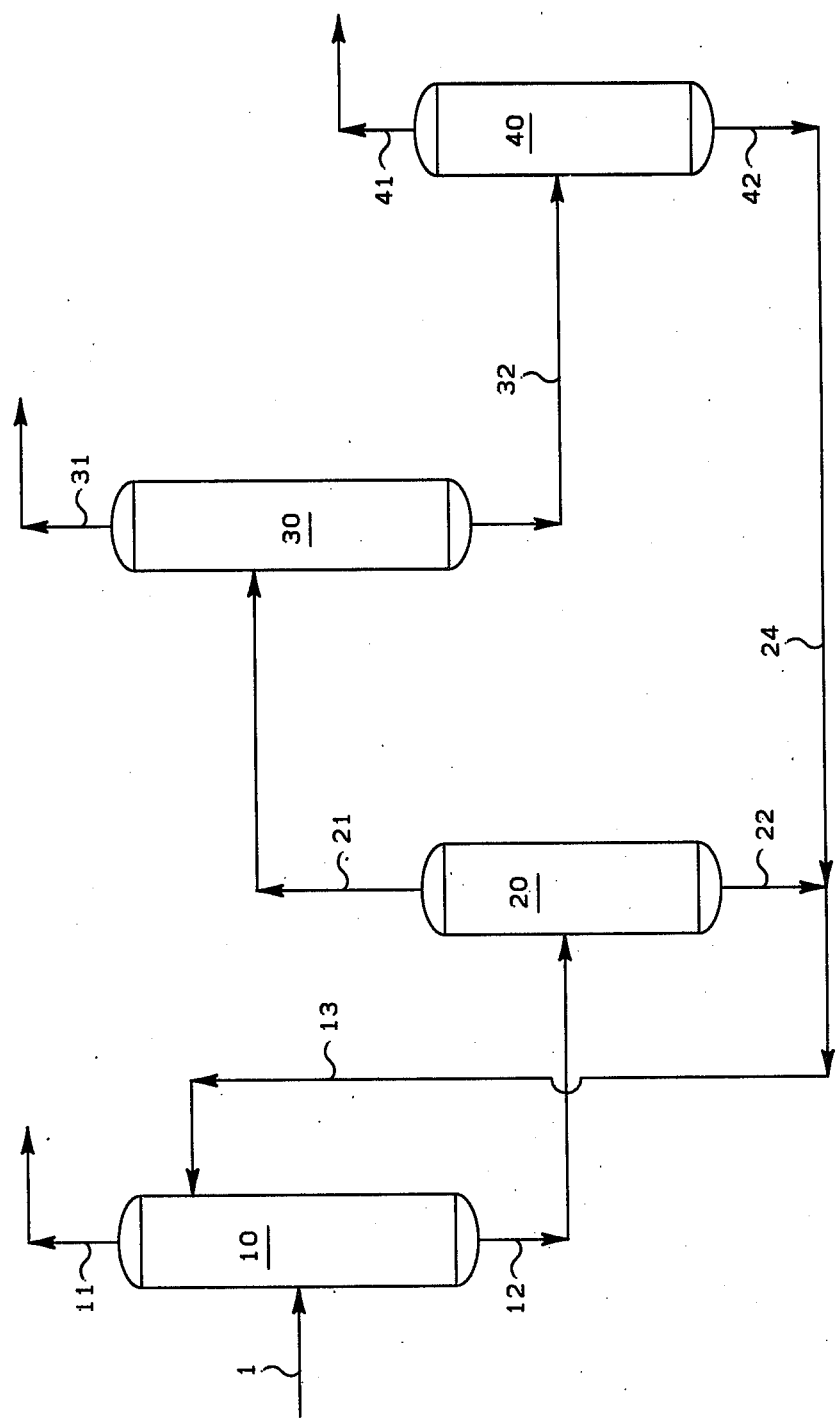

BUTADIENE RECOVERY

The present invention relates to purifying of hydrocarbons. More specifically the present invention relates to the purification of butadiene. One aspect of this invention is a process for separating vinylacetylene from a vinylacetylene-containing butadiene stream.

BACKGROUND OF THE INVENTION

In the production of butadiene, e.g., by dehydrogenation or naphtha cracking, a certain amount of vinylacetylene is generally produced. Since vinylacetylene in many instances is a poison for the catalyst for polymerizing butadiene and since vinylacetylene also constitutes a safety hazard because the compound is unstable in higher concentrations, it is desirable to remove vinylacetylene from the butadiene stream.

THE INVENTION

It is one object of this invention to provide a process for separating vinylacetylene from a mixture of butadiene and vinylacetylene.

Another object of this invention is to provide a relatively pure butadiene product from a multicomponent mixture consisting essentially of hydrocarbon compositions with four carbon atoms.

These and other objects, details, features and embodiments of this invention will become apparent to those skilled in the art from the following detailed description of the invention, the appended claims, the examples and the drawing which is a schematic flow diagram of the process of the invention.

In accordance with this invention, there has been found that when a $C_4$-hydrocarbon feedstock is extractively distilled using a mixture of sulfolane and ketone as the selective solvent to form a rich solvent, when an extract product is stripped from the rich solvent and when the extract product is further fractionated, a very efficient fractionation of the extract product into a butadiene stream and vinylaceytylene stream can be achieved if a portion of the ketone component of the selective solvent is removed from the stripping step together with the extract product and introduced together with this extract product into the fractionation step.

More specifically, this invention consists in a process for producing a relatively pure 1,3-butadiene stream from a feedstock consisting of a mixture of $C_4$-hydrocarbons. This process is characterized by a first step in which the hydrocarbon feedstock consisting essentially of 1,3-butadiene, butane, butenes, and vinylacetylene is extractively distilled utilizing as the selective solvent a mixture of a sulfolane and a ketone selected from the group consisting of acetone, methylethyl ketone and mixtures thereof. In this first step a rich solvent effluent consisting essentially of hydrocarbons, namely 1,3-butadiene, vinylacetylene, and a smaller amount of butenes than the feedstock and the selective solvent, as well as a raffinate effluent is produced. Thereafter the rich solvent effluent is stripped to yield a lean solvent consisting essentially of sulfolane and a first portion of the ketone and an extract product consisting essentially of the hydrocarbons and a second portion of the ketone and being essentially free of sulfolane. This extract product is thereafter further fractionally distilled essentially in the absence of other solvents than the ketone to form an overhead product which consists essentially of butadiene and a bottoms product consisting essentially of vinylacetylene, butene-2's and the ketone. Thus a portion of the ketone (part of the solvent) is intentionally allowed to leave the first solvent stripping step overhead in accordance with this invention.

Further embodiments of this invention comprise one or more of the features disclosed in the following. Reference numerals in the tables in the following refer to the respective items in the drawing.

As shown in the drawing which is a schematic flow diagram for a separation unit in which the process of this invention can be carried out, a feedstream consisting essentially of butane, butenes, butadiene and vinylacetylene is introduced into an extractive distillation column 10 via line 1. A selective solvent consisting of sulfolane and a ketone selected from the group consisting of acetone and methylethyl ketone and mixtures thereof is introduced into the same column 10 above the location of the introduction of the feedstream. From this extractive distillation column 10, a raffinate stream 11 consisting essentially of butane and some butenes is withdrawn. This raffinate stream is essentially free of selective solvent. A rich solvent stream 12 consisting essentially of the selective solvent as introduced via line 13 and butadiene, butenes, and vinylacetylene is withdrawn via line 12.

This rich solvent stream 12 is introduced into a stripper 20 wherein lean solvent which consists essentially of the sulfolane and a first portion of the ketone is removed as a bottom stream via line 22. The conditions in the stripper 20 are such that a portion of the ketone is intentionally removed overhead via line 21 so that the extract product stream in line 21 is composed essentially of butadiene, vinylacetylene, a small quantity of butenes and ketone.

Stream 21 is introduced into a fractionation column 30 from which an overhead stream 31 consisting essentially of butadiene and a bottom stream 32 consisting essentially of ketone, vinylacetylene and butenes is withdrawn.

The bottom stream 32 is then introduced into a separation zone 40 from which stream 41 comprising butenes and vinylacetylene is removed overhead and a ketone stream is removed via line 42 from the bottom of the separation zone 40. The ketone stream from line 42 passes through line 24 and is combined with the lean solvent leaving the stripper 20 via line 22 and then reintroduced into the extractive distillation column 10 via line 13.

While for the sake of clarity and simplicity, the reboiler and reflux means which are present in the four units 10, 20, 30 and 40, as well as valves and pumps, etc., have not been shown in the drawing, it is to be understood that each one of these units is provided with a reboiler and with a reflux unit. The reflux unit comprises a cooler and knockout drum, as well as a pump, which pumps part of the liquid collected in the knockout drum back into the uppermost portion of the columns. The balance of the liquid is passed on to the various other locations shown.

In the separation process of this invention wherein a hydrocarbon feedstock is first extractively distilled with a sulfolane/ketone solvent, the extract is then stripped to let some ketone go overhead with the butadiene and vinylacetylene, and to remove all the sulfolane from the bottom, and wherein this overhead containing some ketone is then fractionated as described, the feedstock composition and fractionation conditions are preferably within the ranges shown in the following tables.

TABLE 1

Composition of C₄-Hydrocarbon Feedstock (parts by weight) (stream 1)

| | |
|---|---|
| Butane | 6–10 |
| Butene-1 | 29–14 |
| trans-Butene-2 | 8–5 |
| cis-Butene-2 | 8–5 |
| Total butenes | 45–24 |
| 1,3-Butadiene | 40–66 |
| Vinylacetylene | 0.05–0.5 |

TABLE 2

Conditions of the Extractive Distillation Using Sulfolane/Ketone as the Extractive Solvent (Unit 10)

| | | |
|---|---|---|
| Temperatures, °F. (°C.) | | |
| Top | 160–170 | (71–77) |
| Bottom | 212–260 | (100–127) |
| Feedstock | 120–130 | (49–54) |
| Solvent | 140–160 | (60–71) |
| Pressure, psig (kPa) | | |
| Top | 83–93 | (675–745) |
| Bottom | 85–95 | (690–758) |
| Number of Trays | 140 | (19–46 theo.) |
| Reflux (wt. ratio) | | |
| Reflux to overhead | 3/1–15/1 | |
| Reflux to feedstock | 1.2/1–2.3/1 | |
| Solvent | | |
| Composition sulfolane/ketone (wt. %) | | |
| Sulfolane | 60–90 | |
| Ketone | 40–10 | |
| Solvent/C₄-hydrocarbon feedstock mass flow rate | 6/1–8/1 | |

TABLE 3

Typical Operation Data of Stripper 20 to Achieve Carryover of 1 to 10 wt. % of the Total Ketone in the Overhead

| | | |
|---|---|---|
| Temperature, °F. (°C.) | | |
| Top | 113–180 | (45–82) |
| Bottom | 290–300 | (143–149) |
| Feed 12 | 85–120 | (29–49) |
| Pressure, psig (kPa) | | |
| Top | 49–79 | (441–648) |
| Bottom | 50–80 | (448–655) |
| Reflux | | |
| Reflux/feed | 0.04–0 | |
| Reflux/overhead | 0.8–0 | |

The butadiene/vinylacetylene mixture that is fractionally distilled in accordance with this invention in the presence of the ketone that is allowed to leave the stripper overhead contains a small quantity of vinylacetylene. The usually employed composition of this butadiene/vinylacetylene mixture and a typical composition are shown in the following table which also shows the ketone content.

TABLE 4

Composition of Butadiene/Vinylacetylene Mixture (stream 21)

| | Range of Usually Employed Composition (wt. % MEK-free) | Typical Composition (wt. %) |
|---|---|---|
| 1,3-Butadiene | (55–98) | 90.0 |
| Vinylacetylene | (0.01–0.20) | 0.1 |
| Butene-1 | (0.2–2.0) | 1.0 |
| cis-Butene-2 | (0.5–10) | 6.4 |
| trans-Butene-2 | (0.2–5) | 2.5 |
| Total butenes | (2.0–15) | 9.4 |
| Ketone[1] | 1–10 | 5[1] |

[1]Parts by weight per part by weight of butylenes.

The conditions in the fractional distillation step will normally be as shown in Table 5.

TABLE 5

Fractionation Conditions for Butadiene Concentrate in the Presence of a Ketone (Unit 30)

| | | |
|---|---|---|
| Temperature, °F. (°C.) | | |
| Top | 110–115 | (43–46) |
| Bottom | 130–145 | (54–63) |
| Feedstock | 100–115 | (38–46) |
| Pressure, psig (kPa) | | |
| Top | 58–63 | (504–538) |
| Bottom | 60–65 | (516–551) |
| Number of Trays (or equivalent) | 200 | (48 theo.) |
| Reflux (wt. ratio) | | |
| Reflux/overhead | 7/1–12/1 | |
| Reflux/feed | 6/1–10/1 | |

The invention will be more fully understood from the following examples, which are intended to illustrate yet further preferred embodiments of this invention, but not to unduly limit the scope thereof.

EXAMPLE I

In the following example, four runs were carried out in which a butadiene concentrate of a given composition was fractionated in a 4″ (0.10 m) diameter column having 140 sieve trays. The feedstock composition, the overhead composition, the bottoms composition, as well as the fractionation conditions, are shown in detail in the following table.

TABLE 6

Fractionation of Butadiene Concentrate

| Run No. | 1 | 2 | 3 | 4 |
|---|---|---|---|---|
| Feed Tray | 48 | 48 | 48 | 48 |
| Flow Rates, lb/hr | | | | |
| Feed | 15 | 15 | 25 | 25 |
| Reflux | 150 | 150 | 150 | 150 |
| Overhead Product | 12.5 | 11.0 | 21.6 | 17.6 |
| Bottoms Product | 2.5 | 4.0 | 3.4 | 7.4 |
| Reflux Ratio | | | | |
| Reflux/Overhead | 12.0 | 13.6 | 6.9 | 8.5 |
| Reflux/Feed | 10.0 | 10.0 | 6.0 | 6.0 |
| Compositions, wt. % | | | | |
| Feed (21) | | | | |
| Butene-1 | 0.40 | 0.38 | 0.41 | 0.36 |
| trans-Butene-2 | 3.24 | 4.00 | 3.00 | 4.08 |
| cis-Butene-2 | 9.01 | 12.20 | 7.35 | 12.46 |
| 1,3-Butadiene | 86.75 | 76.64 | 88.74 | 74.79 |
| Vinylacetylene | 0.040 | 0.065 | 0.050 | 0.066 |
| Acetone | 0.60 | 7.79 | 0.49 | 8.31 |
| Overhead (31) | | | | |
| Butene-1 | 0.47 | 0.50 | 0.46 | 0.54 |
| trans-Butene-2 | 0.24 | 0.20 | 0.99 | 0.27 |
| cis-Butene-2 | 0 | 0 | 0.07 | 0 |
| 1,3-Butadiene | 99.28 | 99.30 | 98.48 | 99.19 |
| Vinylacetylene | 0.006 | 0.004 | 0.027 | 0.004 |
| Acetone | 0.008 | 0.018 | 0.007 | 0.01 |
| Bottoms (32) | | | | |
| Butene-1 | 0 | 0 | 0 | 0 |
| trans-Butene-2 | 17.70 | 13.20 | 15.80 | 13.17 |

TABLE 6-continued

| Fractionation of Butadiene Concentrate | | | | |
|---|---|---|---|---|
| Run No. | 1 | 2 | 3 | 4 |
| cis-Butene-2 | 53.90 | 43.38 | 54.81 | 43.79 |
| 1,3-Butadiene | 25.30 | 14.69 | 26.35 | 16.97 |
| Vinylacetylene | 0.237 | 0.213 | 0.199 | 0.210 |
| Acetone | 3.19 | 28.70 | 3.04 | 26.07 |
| Butadiene Recovered in Overhead, % | 95.4 | 95.0 | 95.9 | 93.4 |
| Temperatures, °F. | | | | |
| Feed | 115 | 104 | 114 | 109 |
| Reflux | 107 | 110 | 108 | 109 |
| Kettle | 132 | 142 | 132 | 142 |
| Top Tray | 113 | 110 | 115 | 113 |
| Kettle Pressure, psig | 64 | 64 | 64 | 63 |

The runs that are comparable are Runs 1 and 2 and Runs 3 and 4 which differ essentially in the quantity of acetone present in the feedstock. Runs 1 and 2 as compared to Runs 3 and 4 differ essentially in the severity of reflux and thus in the quantity of vinylacetylene that is allowed to leave the column overhead.

The data of Table 6 clearly show that the presence of about 8 wt. % of acetone in Run 2 as compared to 0.6 wt.% of acetone in Run 1 results in a reduction of the vinylacetylene concentration that leaves the fractionation column overhead, together with the butadiene product from 60 ppm vinylacetylene to 40 ppm vinylacetylene. The acetone thus achieved a very considerable and desirable reduction in vinylacetylene carry-over of about ⅓ in the product stream, although the vinylacetylene concentration in the feedstock of Run 1 was much lower than in the feedstock of Run 2. Similarly, comparing the results of Runs 3 and 4, it can be seen that approximately 8% acetone in the feedstock as compared to 0.5 wt. % acetone achieved a reduction of the vinylacetylene carryover from 270 ppm to only 40 ppm, again with a higher vinylacetylene concentration in the feedstock of Run 4 as compared to Run 3.

In addition, the four runs also show that the butadiene concentration in the bottoms stream 32 is considerably reduced by utilizing acetone in the fractionation of this invention. In Run 2 the butadiene concentration in the bottoms stream is reduced from about 25 to about 15% comparing Runs 2 and 1. Similarly, the butadiene concentration in the bottoms stream in Run 4 is only about 17% whereas the butadiene concentration in the bottoms stream without added acetone is about 26 wt. %.

The figures given as butadiene recovered in overhead show that although some 8% of the feedstock is acetone, the butadiene recovered in the overhead percentagewise remains essentially unchanged.

EXAMPLE II

A further series of comparative runs for fractional distillation of a typical C$_4$-feed composition were made utilizing in Run 5 no extractive solvent, in Run 6 methylethyl ketone as the extractive solvent, and in Run 7 furfural as the extractive solvent. The feed composition and the results obtained are shown in the following Table 7.

TABLE 7

| Feedstock (wt. %) | |
|---|---|
| Butene-1 | 23.3 |
| t-Butene-2 | 9.8 |
| c-Butene-2 | 5.4 |
| 1,3-Butadiene | 54.4 |
| Vinylacetylene | 0.1 |

Results:

TABLE 7-continued

| Run | 5 | 6 | 7 |
|---|---|---|---|
| Extractive solvent | None | MEK[1] | Furfural |
| Hydrocarbon feed rate, lb/hr | 25 | 18 | 18 |
| Kettle temp., °F. | 156 | 250 | 190 |
| Column pressure, psia | 105 | 85 | 87 |
| Reflux ratio, R/D | 9.6 | 7.0 | 6.8 |
| Solvent/feed ratio (wt.) | — | 1.0 | 1.0 |
| Vinylacetylene rejection[2] | 28.6 | 54.4 | 46.3 |
| Butene-1 rejection, % | 4.4 | 0.2 | 0.1 |
| t-Butene-2 rejection, % | 96.9 | 23.9 | 43.8 |
| c-Butene-2-rejection, % | 100.0 | 95.1 | 68.6 |
| Butadiene rejection (loss), % | 10.7 | 3.0 | 2.4 |

[1]Methylethyl ketone.
[2]Percent of the component in the feed rejected in bottoms product. Butadiene is overhead product.

The results of the comparative runs shown above demonstrate that methylethyl ketone (MEK) as an extractive solvent results in a considerably higher vinylacetylene rejection and a considerably lower butadiene loss as compared to ordinary distillation. The vinylacetylene rejection utilizing MEK also is substantially higher than the value for the furfural solvent.

Reasonable variations and modifications which will become apparent to those skilled in the art can be made in this invention without departing from the spirit and scope thereof.

We claim:

1. A process for producing a purified 1,3-butadiene stream comprising
    a. extractively distilling a hydrocarbon feedstock consisting essentially of 1,3-butadiene, butane, butenes and vinylacetylene utilizing a mixture of sulfolane and a ketone selected from the group consisting of acetone, methylethyl ketone and mixtures thereof as the extractive solvent to form a rich solvent effluent consisting essentially of hydrocarbons, namely 1,3-butadiene, vinylacetylene and a smaller amount of butenes than the feedstock and the selective solvent, as well as a raffinate effluent,
    b. stripping the rich solvent effluent under conditions sufficient to yield a lean solvent consisting essentially of sulfolane and a first portion of the ketone and an extract product consisting essentially of the hydrocarbons and a second portion of the ketone wherein said second portion of ketone is an amount sufficient to improve the subsequent separation of 1,3-butadiene and vinylacetylene, and
    c. fractionally distilling said extract product to form an overhead product which consists essentially of 1,3-butadiene as said purified butadiene stream and a bottom product comprising vinylacetylene, ketone and butenes.

2. A process in accordance with claim 1 wherein said feedstock contains less than about 0.5 wt. % of vinylacetylene.

3. A process in accordance with claim 1 wherein said selective solvent is composed of about 60–90 wt. % sulfolane and about 40–10 wt. % of said ketone.

4. A process in accordance with claim 1 wherein said extract product contains about 1 to about 10 parts by weight of said ketone per part by weight of said butenes.

5. A process in accordance with claim 1 wherein said bottom product consisting essentially of a vinylacetylene, butene-2 and said ketone is introduced into a separation zone from which a first stream of butene-2 and vinylacetylene and being essentially free of said ketone and a second stream consisting essentially of said ketone and being essentially free of vinylacetylene are removed.

6. A process in accordance with claim 5 wherein said second stream and said lean solvent are reintroduced into step (a) as selective solvent.

* * * * *